United States Patent
Pinza et al.

[11] Patent Number: 6,043,285
[45] Date of Patent: Mar. 28, 2000

[54] USE OF P-AMINOPHENOL DERIVATIVES FOR THE PREPARATION OF PHARMACEUTICAL COMPOSITIONS USEFUL IN THE TREATMENT OF NEURODEGENERATIVE DISEASES

[75] Inventors: Mario Pinza, Corsico; Mario Brufani, Castel; Claudio Milanese, Rome, all of Italy

[73] Assignee: Angelini Ricerche S.p.A. Societa'Consortile, S. Palomba-Pomezia, Italy

[21] Appl. No.: 09/147,280

[22] PCT Filed: May 15, 1997

[86] PCT No.: PCT/EP97/02708

§ 371 Date: Feb. 5, 1999

§ 102(e) Date: Feb. 5, 1999

[87] PCT Pub. No.: WO97/44020

PCT Pub. Date: Nov. 27, 1997

[30] Foreign Application Priority Data

May 21, 1996 [IT] Italy .................... MI96A1013

[51] Int. Cl.[7] .................... A61K 31/135; A61K 31/16
[52] U.S. Cl. .................... 514/649; 514/616; 514/647
[58] Field of Search ................. 514/616, 649, 514/647

[56] References Cited

U.S. PATENT DOCUMENTS

| | | | |
|---|---|---|---|
| 5,643,960 | 7/1997 | Breitner et al. | 514/570 |
| 5,756,548 | 5/1998 | Flitter et al. | 514/616 |

FOREIGN PATENT DOCUMENTS

WO-95/28153 of 1995 WIPO .

OTHER PUBLICATIONS

Martindale, The Extra Phamacopoeia, Thirtieth Edition, pp. 2, 27–28 (1993).

Neurobiology of Aging, vol. 16 (4), pp. 523–530; J.C.S. Breitner et al. (1995).

*Primary Examiner*—Theodore J. Criares
*Attorney, Agent, or Firm*—Oblon, Spivak, McClelland, Maier & Neustadt, P.C.

[57] ABSTRACT

A therapeutic method comprising treating a patient suffering from a neurodegenerative disease with a therapeutically effective quantity of a p-aminophenol derivative.

6 Claims, No Drawings

USE OF P-AMINOPHENOL DERIVATIVES FOR THE PREPARATION OF PHARMACEUTICAL COMPOSITIONS USEFUL IN THE TREATMENT OF NEURODEGENERATIVE DISEASES

This application is a 371 of PCT/EP97/02708 filed May 15, 1997.

The present invention concerns the use of p-aminophenol derivatives for the preparation of pharmaceutical compositions useful in the treatment of neurodegenerative diseases.

More particularly, the present invention concerns the use of derivatives of p-aminophenol and prodrugs thereof for the preparation of pharmaceutical compositions useful in the treatment of neurodegenerative diseases which contain an inflammatory component with production in loco of inflammatory markers such as proteins of the complement and cytokines.

Still more particularly, the present invention concerns the use of compounds having the formula

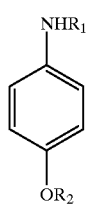

(I)

wherein
$R_1$ is hydrogen or lower acyl, and
$R_2$ is hydrogen or lower alkyl
and the use of prodrugs thereof.

Typical examples of such compounds are phenacetin ($R_1$=COCH$_3$; $R_2$=C$_2$H$_5$), also known as acetophenetidine, and paracetamol ($R_1$=COCH$_3$; $R_2$=H), also known as acetaminophen or N-acetyl-p-aminophenol.

Typical examples of prodrugs are propacetamol (B. Bannwarth et al., "Br. J. Clin. Pharmac.", 34, 79–81, 1992), acetaminosalol (R. Q. Brewster, "J. Am. Soc.", 40, 1136, 1918) and its glycine ester (I. M. Kovach et al., "J. Pharm. Sci.", 64, 1070, 1975). With regard to use of the term "prodrug", the reader is referred to "Burger's Medicinal Chemistry and Drug Discovery—Vol. 1; Principles and Practice—5th ed.—Ed. Manfred E. Wolff—pp. 172–178".

It is already known that these compounds possess analgesic and antipyretic actions comparable to those of aspirin, whilst unlike acetylsalycylic acid they possess no significant anti-inflammatory action (Insel A. P. in: "The Pharmacologic basis of therapeutics" Goodman Gilman A. et al. ed., pp. 656–659, Pergamon Press, 1990).

Because of its general toxicity and side effects, phenacetin is currently little used for therapeutic purposes.

Paracetamol however is well tolerated and presents no significant side effects in low therapeutic doses from 0.5 to 1 g, 3 or 4 times a day.

Paracetamol is rapidly absorbed and is distributed evenly throughout the major part of the tissues of the organism, including the brain. The plasma concentration reached within a few minutes of oral administration of 1 g paracetamol is approximately 10 mg/l (66.2 $\mu$M) and increases to approximately 1.5 mg/l after 6 hours. The tissue concentration is substantially the same as the plasma concentration (Prescott L. F., "Br. J. Clin. Pharmacol.", 10 (suppl. 2), 291–298S, 1980).

The mode of action of paracetamol is not yet fully known. It is however generally agreed that its activity is dependent on its ability to inhibit prostaglandin production mainly in the central nervous system. This action would appear to explain the analgesic and antipyretic effects of paracetamol. The absence of action on peripheral cycloxygenase could, on the other hand, be responsible for its lack of anti-inflammatory action (Clissold, S. P., "Drugs", 32 (suppl. 4), 46–59, 1986).

Alzheimer's disease is a pathology characterised by progressive neurodegeneration leading to dementia. Autopsy examination constantly reveals certain typical histological markers such as plates due to excessive deposition of β-amyloid and loss of neurons and/or synapses (Selkoe D. J. et al., "Neuron", 6, 487–493, 1991).

In recent years the presence of inflammation markers in cerebral samples from patients suffering from Alzheimer's disease has been documented with increasing frequency. Proteins typical of inflammatory processes such as antigens of histocompatibility, certain cytokines and their receptors, Fc receptors, certain proteins of the acute phase and proteins of the classic pathway of activation of the complement together with their receptors have in fact been identified in amyloid plates or in the region of such plates (Dickson D. W. et al., "Glia", 7, 75–83, 1993). It has also been demonstrated that such inflammatory proteins are secreted in loco by glial cells and microglial cells (Hugh Perry V. et al., "Trends Neurol. Sci.", 7, 268–273, 1993). A minor incidence of this pathology in patients suffering from rheumatoid arthritis who need anti-inflammatory drugs for long periods of time has also been proved with adequate clarity (McGeer P. L. et al., "Neurology", 42, 447–449, 1992; Breitner J. S. et al., "Neurology", 44, 227–232, 1994; Rogers J. et al., "Neurology", 43, 1609–1611, 1993).

In particular, a double blind study of 44 patients suffering from Alzheimer's disease treated with indomethacin for 6 months has shown a notable slowing of the progression of dementia in comparison with control subjects treated with a placebo (Schnabel J., "Science", 260, 1719–1720, 1993). These observations indicate that the "cerebral inflammatory" phenomena typical of Alzheimer's disease are not simply a reaction to the pathological phenomenon already in progress, but that the said cerebral inflammatory phenomena themselves become a pathogenic factor of primary significance.

J. C. S. Breitner et al. (Neurobiology of aging, Vol. 16(4), 1995, pages 523–530) refer about a retrospective investigation on subjects who had taken paracetamol for treating pain and fever. Although, the pharmaceutical preparations previously administered to the subjects had not been manufactured to treat the Alzheimer disease, this investigation had the aim of discovering whether the treatment with paracetamol had cause a statistically significant delay in the onset of the Alzheimer disease. The result was negative.

WO-A-9528153 discloses a group of 11 specific benzamide compounds for treating neurodegenerative diseases. The activity of these compounds is said to be unexpected and not predictable based on the fact that other, structurally closely related materials lack activity. Slight structural changes are reported to yield large differences in efficacy and toxicity.

It has now unexpectedly been found that the compounds of formula (I) and prodrugs thereof are useful in the treatment of neurodegenerative diseases in which an inflammatory component is present with in loco production of proteins of the complement and cytokines, despite the fact that such compounds possess no anti-inflammatory action.

In particular, the said compounds inhibit the production of proteins of the complement and cytokines by glial brain cells and allow a significant reduction of the inflammatory phenomena typically present in the brain of patients suffering from Alzheimer's disease.

The purpose of the present invention therefore consists of the use of a compound having the formula

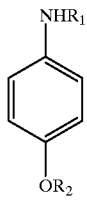
(I)

wherein $R_1$ is hydrogen or lower acyl, and $R_2$ is hydrogen or lower alkyl, and prodrugs thereof for the preparation of a pharmaceutical composition useful in the treatment of neurodegenerative diseases in which there is present an inflammatory component with in loco production of inflammatory markers such as proteins of the complement and cytokines.

A typical example of such disorders is Alzheimer's disease.

In the course of the present description and of the claims which follow, the expression "proteins of the complement" indicates a complex of approximately 20 proteins which make up the complement system, and which possess an inflammatory action of cascade catalysis type. Activation of the system, which can take place in two ways known as the direct or alternative activation pathways, leads, in the end, to cellular lysis.

Some of the factors (proteins) are designated with the letter "C" followed by a number, and the most important and abundant component is the factor known as C3 (I. M. Roitt, in: Immunologia; fisiologia, patologia o clinica; italian ed. by C. E. Grossi and D. Zarcone, page 7, Edi-Ermes, Milano, 1990) [Immunology; physiology, pathology or clinic; Italian edition by C. E. Grossi and D. Zarcone, page 7, Edi-Ermes, Milan, 1990]. In experiments for the purpose of assessing possible production of proteins of the complement therefore, only C3 is determined and is considered indicative of the entire complex of proteins of the complement.

The cytokines are a family of proteins which have the function of enabling communication between the various cell types which form part of the immune system and consequently of regulating the various aspects of the immune response, including inflammatory phenomena. Amongst the cytokines predominately involved in inflammatory response, interleukin-6 (IL-6) performs a role of primary importance: such a cytokine is in fact produced by numerous cell types (macrophages, B and T lymphocytes, endothelial cells) and controls immune response, acute phase reactions and haematopoiesis. Raised levels of IL-6 are regarded as indicative of an inflammatory reaction taking place and have been found in numerous pathologies which have an inflammatory component, such as rheumatoid arthritis and systemic lupus erythematosus.

The daily dose of the compound according to formula (I) can vary within a rather wide range depending on known factors such as the type and severity of the disease, the patients body weight, the pharmaceutical composition used, the method of administration, the number of dosage forms administred daily and the effectiveness of the compound used.

The optimum dose can nevertheless easily be established by an expert in the field by routine procedures.

Generally speaking, the daily dose will be between 0.01 and 200 mg/kg.

In the particular case of paracetamol, the daily dose will preferably be of from 10 to 100 mg/kg or, even more preferably, of from 15 to 75 mg/kg.

Examples of suitable methods of administration are: oral, rectal and injection.

Depending on the administration methods chosen, the pharmaceutical compositions according to the present invention may be in solid form, for example tablets, coated tablets, capsules and controlled release compositions or semi-solid form, for example suppositories, or in liquid form for example sterile solutions. Examples of controlled release compositions are those which include liposomes or vesicles (capable of releasing the pharmacologically active compound in a controlled manner) and layered tablets comprising layers with variable disintegration speeds.

In addition to the usual excipients, the compositions may include additives suitable for pharmaceutical use such as preservatives, stabilisers, surfactants, emulsifiers, salts to regulate osmotic pressure, buffers, flavourings, sweeteners, colourings and the like.

The compositions according to the present invention may contain other compatible active principles which may be therapeutically useful when used simultaneously. Such compounds include: antioxidants such as acetylcysteine, vitamin E, glutathione and methionine, calcium antagonists, glutamate antagonists for NMDA receptors such as dextromethorphan, acetylcholine receptor agonists, in particular muscarine or nicotine agonists, and pharmaceuticals capable of acting on the nervous system by increasing acetylcholine levels at synaptic level (acetylcholinesterase inhibitors). Examples of suitable compounds which are active on the cholinergic system are tacrine, physostigmine, neostigmine, heptastigmine, donepezil (E-2020), metriphonate and SDZ-ENA-713.

The pharmaceutical compositions according to the present invention can be produced by conventional chemicopharmaceutical methods comprising mixing, granulation and compression, when necessary, or various mixtures and dissolution of the ingredients depending on which is the most suitable to produce the required product.

The following examples serve to illustrate the present invention, but are not limitative.

EXAMPLE 1

Paracetamol and indomethacin activity on complement production in the T98G cell line The effect of paracetamol on the production of complement factors has been studied using the human glioblastoma T98G cell line. The said line is in fact capable of constitutively producing factor 3 of the complement (C3) and this synthesis is further increased in the presence of various stimuli such as interleukin-1 beta (IL-1β). Indomethacin has been used as the reference drug.

The cells ($2 \times 10^6$/ml) were incubated for 48 hours in the presence of increasing concentrations of paracetamol (10–100–500–1000 μM) or indomethacin (0, 1–1–10 μM) both in the presence and in the absence of IL-1β (50 U/ml). On completion of incubation, the culture medium was harvested and the quantity of C3 secreted by the cells in the various conditions was measured. C3 was assayed in a sandwich-type immunoenzymatic test, in which two anti-C3 antibodies of different species were used as well as an antiserum labeled with an alkaline phosphatase specific for one of the two anti-C3 antibodies. The secreted C3 was quantified using a standard curve prepared on the basis of purified C3.

The results (Table 1) show that paracetamol inhibits the secretion of C3 with a $Cl_{50}$ of approximately 1 mM both when the cells are stimulated with interleukin-1 beta and in the absence of the said cytokine. Indomethacin was found to be active in reducing the secretion of the complement in this test but, because of its toxicity in the cellular system used, it was not possible to increase its concentration above 10 µM, at which dose it shows a 35% inhibiting activity.

These results indicate that both paracetamol and indomethacin are capable of reducing secretion of factors of the complement which occurs in the brain in pathological conditions.

These observations testify in favour of the use of paracetamol in pathologies in which significant production of factors of the complement exists in the central nervous system, such as, for example, Alzheimer's disease.

TABLE 1

Activity of Paracetamol and Indomethacin on Production of Complement in the T98G Cell Line

|  | Dose | Inhibition % |
|---|---|---|
| Cell Stimulation with IL-1β |  |  |
| Paracetamol | 1000 µM | 47.5 |
|  | 500 µM | 39.8 |
|  | 100 µM | 23.6 |
|  | 10 µM | 0.1 |
| Indomethacin | 10 µM | 35.1 |
|  | 1 µM | 21.7 |
|  | 0.1 µM | 26.9 |
| Cell not Stimulated with IL-1β |  |  |
| Paracetamol | 1000 µM | 60.8 |
|  | 500 µM | 37.4 |

EXAMPLE 2

Activity of paracetamol and indomethacin on the production of interleukin-6 (IL-6) in the cell line T98G stimulated with β-amyloid The effect of paracetamol on the production of IL-6 was studied using the human cell line glioblastoma T98G. The said line is in fact capable of constitutively producing IL-6 and this synthesis is augmented in the presence of aggregated β-amyloid. Indomethacin was used as the reference drug.

The cells ($2 \times 10^6$/ml) were incubated for 48 hours in the presence of increasing concentrations of paracetamol (10–1000 µM) or indomethacin (0.1–10 µM) in the presence of β-amyloid (50 µM) aggregated by incubation at 37° C. for 6 days. At the end of the experiment the culture medium was harvested and the quantity of IL-6 produced in the various conditions was assayed using a commercial immunoenzymatic kit (Biotrak IL-6, Amersham, UK).

The results (Table 2) show that paracetamol inhibits production of IL-6 with a $Cl_{50}$ of slightly over 1 mM. The inhibiting activity of indomethacin on IL-6 is of from 10 to 20%.

These results indicate that paracetamol is capable of reducing the secretion of IL-6 occurring in the brain in the presence of β-amyloid, a condition typical of Alzheimer's disease, this observation therefore justifies the use of paracetamol in this pathology.

TABLE 2

Activity of Paracetamol and Indomethacin on the Production of IL-6 in the T98G Cell Line

| Cell Stimulation with β-amyloid | Dose | Inhibition % |
|---|---|---|
| Paracetamol | 1000 µM | 41.2 |
|  | 500 µM | 20.5 |
|  | 100 µM | 6.7 |
|  | 10 µM | 11.4 |
| Indomethacin | 10 µM | 11.5 |
|  | 1 µM | 17.6 |
|  | 0.1 µM | 21.1 |

EXAMPLE 3

Activity of paracetamol and indomethacin on the production of prostaglandins in the T98G and J774.2 cell lines The benefit of paracetamol in cerebral inflammatory pathologies has been confirmed by other experiments designed to demonstrate that paracetamol possesses a selectivity of action in respect of brain cells which is not found for other anti-inflammatory drugs, such as indomethacin.

Parallel experiments were conducted in which the ability of paracetamol and indomethacin to inhibit the production of prostaglandins produced by the glioblastoma T98G cell line or by the J774.2 cellular macrophagic cell line was assessed.

The test with T98G cells stimulated with IL-1β was conducted as described in the previous Example 1. At the end of incubation the culture medium was harvested and the quantity of E2 prostaglandins present was measured. The prostaglandins were assayed by means of a commercially available immunoenzymatic test (AMERSHAM).

The results given in Table 3 show that paracetamol and indomethacin are both capable of inhibiting production of prostaglandins in the glial cells of the central nervous system in a significant manner.

TABLE 3

Activity of Paracetamol and Indomethacin on Production of prostaglandins in the T98G cell line

| Cell Stimulation with IL-1β | Dose | Inhibition % |
|---|---|---|
| Paracetamol | 1000 µM | 99 |
|  | 500 µM | 96.9 |
|  | 100 µM | 88.5 |
|  | 10 µM | 26.7 |
| Indomethacin | 10 µM | 99.1 |
|  | 1 µM | 98.4 |
|  | 0.1 µM | 99.3 |

Parallel to the above experiment, J774.2 ($2 \times 10^6$/ml) macrophagic cells were stimulated with lipopolysaccharide (LPS) (1 µg/ml) for 12 hours. After 3 washes with physiological solution, the cells were incubated for 45 minutes together with increasing concentrations of paracetamol (0.1–100 µM) or indomethacin (0.01–1 µM). At the end of incubation the supernatants were harvested and the prostaglandin E2 content was measured using the previously described test.

The results given in Table 4 indicate that paracetamol, contrary to indomethacin, has little inhibiting activity on production of prostaglandins in macrophages, and hence in cells situated outside the central nervous system.

TABLE 4

Activity of Paracetamol and Indomethacin on Production of Prostaglandins in the J744.2 Cell Line

| Cell Stimulation with LPS | Dose | Inhibition % |
|---|---|---|
| Paracetamol | 100 μM | 11.4 |
|  | 10 μM | 12.5 |
|  | 1 μM | 6.4 |
|  | 0.1 μM | 5.3 |
| Indomethacin | 1 μM | 87.4 |
|  | 0.1 μM | 61.1 |
|  | 0.01 μM | 35.8 |

The data in Tables 1, 2, 3 and 4 as a whole demonstrate that paracetamol, contrary to indomethacin, possesses a peculiar selectivity of action on the nervous system, which makes the drug particularly useful in the treatment of Alzheimer's disease.

What is claimed is:

1. A therapeutic method comprising treating a patient suffering from a neurodegenerative disease with a therapeutically effective quantity of a compound having the formula

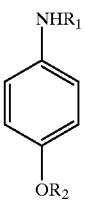
(I)

wherein
$R_1$ is hydrogen or lower acyl, and
$R_2$ is hydrogen or lower alkyl
or a prodrug thereof.

2. A method according to claim 1, wherein the neurodegenerative disease is Alzheimer's disease.

3. A method according to claim 1, wherein the compound having the formula (I) is paracetamol.

4. A method according to claim 1, wherein the treatment comprises daily administration of 0.01–200 mg/kg of a compound having the formula (I) or an equivalent quantity of a prodrug of paracetamol.

5. A method according to claim 1, wherein the treatment comprises daily administration of 10–100 mg/kg of paracetamol or an equivalent quantity of a prodrug thereof.

6. A method according to claim 4, wherein the treatment comprises daily administration of 15–75 mg/kg of paracetamol or an equivalent quantity of a prodrug thereof.

* * * * *